United States Patent [19]

Hanaoka et al.

[11] Patent Number: 4,981,804

[45] Date of Patent: Jan. 1, 1991

[54] METHOD FOR DETERMINATION OF MICROCONSTITUENTS

[75] Inventors: Yuzuru Hanaoka; Takeshi Murayama; Tamizo Matsuura, all of Tokyo, Japan

[73] Assignee: Yokogawa Electric Corporation, Tokyo, Japan

[21] Appl. No.: 479,814

[22] Filed: Feb. 14, 1990

Related U.S. Application Data

[62] Division of Ser. No. 721,563, Apr. 10, 1985.

[30] Foreign Application Priority Data

Apr. 16, 1984 [JP] Japan .................................. 59-76166

[51] Int. Cl.$^5$ ...................... G01N 27/00; G01N 30/02
[52] U.S. Cl. .................................. 436/150; 73/61.1 C; 210/656; 422/70; 436/161; 436/175; 436/178
[58] Field of Search ....................... 422/70; 73/61.1 C; 210/198.2, 656, 659; 436/150, 161, 175, 178

[56] References Cited

U.S. PATENT DOCUMENTS

| | | | |
|---|---|---|---|
| 4,204,952 | 5/1980 | Snyder | 210/659 |
| 4,274,967 | 6/1981 | Snyder | 210/659 |
| 4,454,043 | 6/1984 | Ting et al. | 210/198.2 X |
| 4,533,518 | 8/1985 | Hanaoka et al. | 422/70 |
| 4,536,199 | 8/1985 | Toon | 422/70 X |

FOREIGN PATENT DOCUMENTS

| | | | |
|---|---|---|---|
| 38720 | 10/1981 | European Pat. Off. | 210/656 |
| 180359 | 10/1984 | Japan | 210/198.2 |

OTHER PUBLICATIONS

Snyder et al., "Introduction to Modern Liquid Chromatography", Second Edition, Published by John Wiley & Sons, Inc., New York, 1979, pp. 519–522.

Primary Examiner—Robert J. Hill, Jr.
Attorney, Agent, or Firm—Moonray Kojima

[57] ABSTRACT

A method and apparatus for determining, by use of ion chromatography, a microconstituent contained in a major constituent as impurities present in the major constituent. The invention causes only that portion of the effluent from the detector, shown on an ion chromatograph, that corresponds to the neighborhood of the microconstituent to be led again to the collecting valve. Thus, the microconstituent of the solution can be determined quickly and easily, without reference to the kind of microconstituent being tested.

4 Claims, 6 Drawing Sheets

METHOD FOR DETERMINATION OF MICROCONSTITUENTS

This is a division of application Ser. No. 721,563, filed 4/10/85.

BACKGROUND OF THE INVENTION

1. Field of Invention

This invention relates to a method and apparatus for determining, by ion chromatography, the content of a microconstituent in a major constituent, such as impurities in a main component.

2. Description of the Prior Art

The term "ion chromatography" is used to describe high speed liquid chromatography, as suggested in a publication by H. Small et al in 1975, and is used mainly for the analysis of inorganic ions. This method has been widely accepted and is now utilized in various forms of trace analysis including the analysis of environmental samples.

FIG. 1 illustrates a conventional ion chromatograph which embodies the ion chromatography process. In the diagram, an eluate tank 1a is used for storing an eluate, which is an aqueous solution containing $Na_2CO_3/NaHCO_3$ in a concentration on the order of several mM/liter. A pump 2 forwards the eluate under pressure to a sample inlet device 3 to be described more specifically hereinafter. Sample inlet device 3 is used for admitting (or automatically collecting) a prescribed amount of sample solution, introduced, for example, by a microsyringe, and forwarding the sample solution with the eluate from pump 2, to a separation column 4 packed, for example, with an anion-exchange resin. Column 4 is connected to a cation removing device 5 comprising two adjoining chamber, i.e. a first chamber for passing the effluent originating in separation column 4 and flowing through a wall of a perfluorocarbon sulfonate type cation exchange composition, such as for example, NAFION (proprietary designation of DuPont Company), and a second chamber for passing a scavenger liquid to be described in more detail hereinbelow. A detector 6 is used for passing the effluent from the first chamber of cation removing device 5 and, at the same time, for measuring the electric conductivity of the effluent. A recording meter 7 receives the output signal of detector 6 and describes a chromatogram in response to the output signal. A scavenger liquid tank 1b stores a scavenger liquid formed of a prescribed solvent such as, for example, dodecylbenzene sulfonic acid, which is pumped by pump 9 to forward the scavenger liquid from scavenger liquid tank 1b, under pressure, to the second chamber of the cation removing device 5, and then to a tank 8b for storing the scavenger liquid flowing out the second chamber of device 5. A tank 8a stores the liquid which has undergone measurement in detector 6 after flowing out of detector 6. Usually separation column 4, cation removing device 5, and detector 6 are disposed in a constant temperature bath 10 which is maintained at a prescribed temperature.

In the ion chromatograph above described, when the eluate, $Na_2CO_3/NaHCO_3$, held inside eluate tank 1a is introduced via pump 2, sample inlet device 3, and separation column 4 into cation removing device 5, it is converted therein into $H_2CO_3$ through cation exchange of $Na^+$ to $H^+$. As a result, the electric conductivity of the eluate is lowered and the output signal background of detector 6 is eventually lowered. When the solution to be measured is taken in the prescribed amount and is introduced through sample inlet device 3, it is conveyed by the eluate, taken from reservoir 1a, to separation column 4. Here, the ion species, such as for example, an anion, in the solution to be determined, is chromatographically separated. The effluent from column 4 is again conveyed by the eluate via cation removing device 5 into detector 6. Detector 6 consequently feeds out a signal corresponding to the ion species present in the solution being determined.

When the ion chromatograph of the above description is utilized for the determination of a microconstituent (such as, for example, an anion) present in the solution being tested and when the solution contains a major constituent in a very large concentration besides the microconstituent, the efficiency with which the two constituents are separated from each other is degraded even to the extent of rendering the determination of the microconstituent extremely difficult. To overcome the difficulty, there has been made an attempt to effect the determination of the microconstituent by the use of a so-called selective detector which responds only to the microconstituent and not to the major constituent (hereinafter called "first conventional method")

Also, another suggested solution was to attain the determination of the microconstituent by subjecting the solution being tested to a pretreatment for removing the major constituent from the solution and subjecting the remaining solution to analysis (hereinafter called "second conventional method")

Separately, a so-called fractionation and reintroduction method has been attempted to resolve the problem above mentioned. The method comprises analyzing the solution being tested by an ion chromatograph, fractionating the portion of the effluent from a detector corresponding to the neighborhood of the microconstituent while consulting the signal from the detector, subsequently injecting the fraction with the aid of a syringe into a concentration column, and determining the content of the microconstituent again by the use of the ion chromatograph (hereinafter called "third conventional method").

Unfortunately, the first and second conventional methods are disadvantageous in that they lack general adaptability and have been proven to be practicable only when microconstituents to be determined are specific substances. In the case of the third conventional method, since the amount of the fractionated solution is generally large, the method necessitates use of a concentration column and the resistance offered to the eluate flowing through this concentration column is generally large. In this connection, a suppressor using an ion exchange membrane is deficient in resistance to pressure and, therefore, is easily breakable. Thus, the concentration column which experiences such heavy resistance to the solution cannot be connected to the downstream side of the suppressor. Thus, the third conventional method has suffered from a further disadvantage in that desired automation of the determination by interconnecting a solution collecting valve possessed of the concentration column and a flow path switch valve disposed on the downstream side of the detector through the medium of a connecting pipe is extremely difficult to accomplish.

SUMMARY OF THE INVENTION

Accordingly, an object of the invention is to overcome the aforementioned and other deficiencies of the prior art.

Another object is to provide a method and apparatus for easy and quick determination of a microconstituent present in a solution wherein the microconstituent is present in combination with a major constituent as impurities in the major component.

The aforementioned and other objects are attained in the invention which encompasses method and apparatus for determination of the microconstituents in a major constituent, wherein the portion of the effluent from the detector of the ion chromatograph which corresponds to the neighborhood of the microconstituent (an extremely small portion of the solution) is led again to the solution collecting valve.

DETAILED DESCRIPTION OF PREFERRED EMBODIMENTS.

Figure 1:
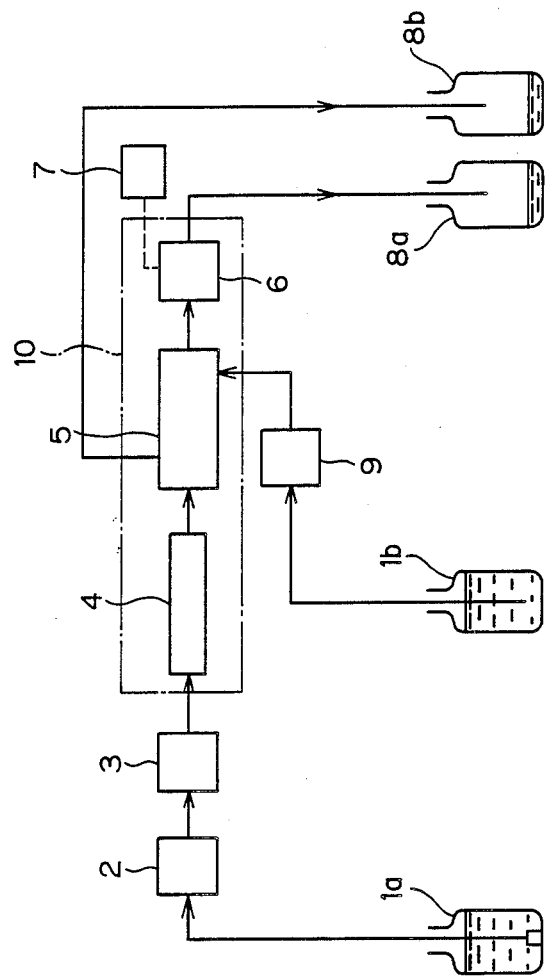
FIG. 1 is an explanatory diagram depicting a conventional ion chromatograph.
Figure 2:
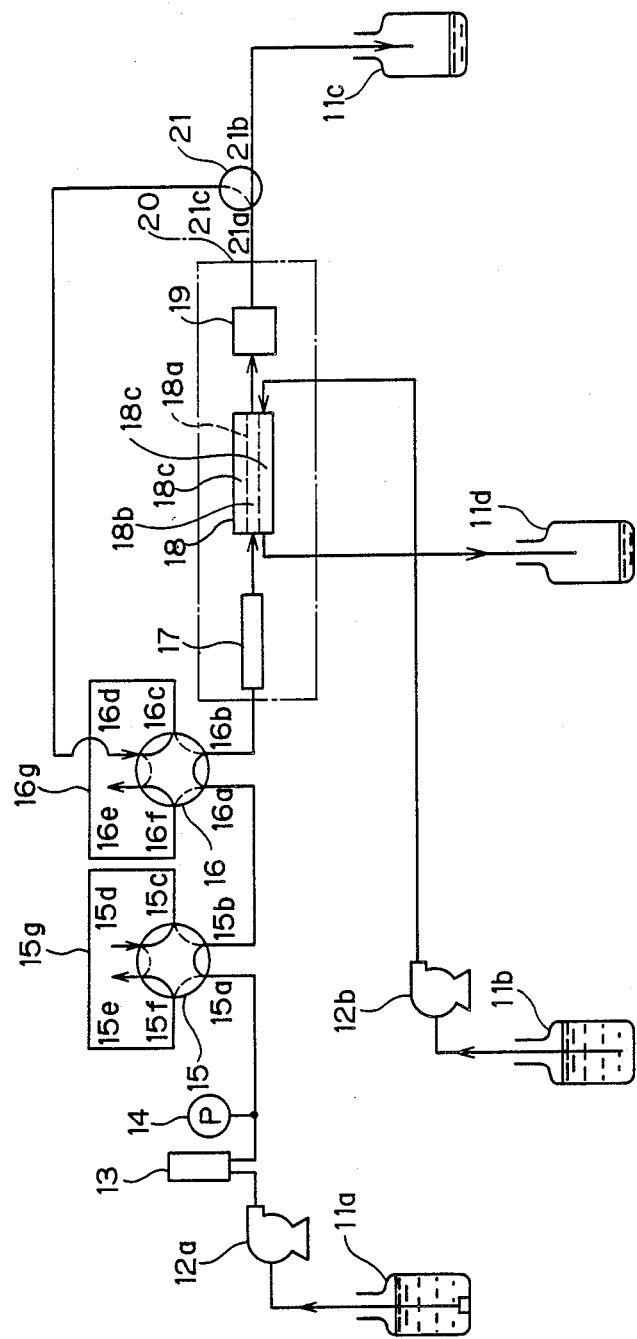
FIG. 2 is an explanatory diagram depicting an illustrative embodiment of the invention.

Turning to FIG. 2, tanks 11a and 11b are used, respectively, for storing an eluate solution and a removing solution, which are pumped respectively, by a liquid feed pump 12a, and 12b. A damper 13 is connected as shown to pump 12 so as to prevent pulsation of the eluate. Pressure gauge 14 is connected as shown. A first sample valve 15 and second sample valve 16 are connected between pump 12a and separation column 17. Valve 15 comprises first through sixth connecting ports 15a–15f and a metering tube 15b and is provided with an internal flow path adapted to be alternately switched between a connected state indicated by solid line and a connected state indicated by the dotted line.

Second sample valve 16 comprises first through sixth connecting ports 16a–16f and a metering tube 16g and is provided with an internal flow path adapted to be alternately switched between a connected state indicated by the solid line and a connected state indicated by the dotted line.

Separation column 17 is packed, for example, with an anion-exchange resin, and is connected to a suppressor 18, which comprises a double tube construction having the interior thereof divided with a tube 18a made, for example, of a cation exchange membrane, into an internal chamber 18b and an external chamber 18c. The effluent is then applied to a detector formed, for example, of an electric conductivity meter. A constant temperature bath 20 is provided for accommodating therein separation column 17, suppressor 18, and detector 19, and maintains these components at a prescribed temperature. A switch valve 21 comprises first through third connection ports 21a–21c and is provided with an internal flow path adapted to to be alternately switched between a connected state indicated by the solid line and a connected state indicated by the dotted line. The valve 21 may be connected to valve 16 as depicted. Waste solution tank 11d, for the removing solution, and 11c for the effluent are connected as depicted. In most cases, the liquids discharged through the fifth connection ports 15e, 16e, respectively, of the first and second sample valves 15, 16, are led into some other waste liquid tanks, not shown.

In the illustrative embodiment, as liquid feed pump 12a is operated, the eluate held inside tank 11a is caused to flow through a path comprising liquid feed pump 12a→damper 13→pressure gauge 14→first and second connection ports 15a, 15b of first sample valve 15→first and second connection ports 16a, 16b of second sample valve 16→separation column 17→internal chamber 18b of suppressor 18→detector 19→first and second connection ports 21a, 21b of switch valve 21→waste solution tank 11c.

As the liquid feed pump 12b is operated, the removing solution held in tank 11b is caused to flow through a path comprising liquid feed pump 12b→external chamber 18c of suppressor 18→waste solution tank 11d. In the state consequently assumed, the solution being tested which contains, for example, 1000 ppm of $Cl^{31}$ ion as the major constituent and 15 ppm of $NO_2^-$ ion as the microconstituent is introduced via fourth connection port 15d of first sample valve 15 into metering tube 15g. Then, first sample valve 15 is turned ON to shift the internal flow path thereof from the connected state indicated by the solid line to the connected state indicated by the dotted line, as shown in FIG. 2.

The solution being tested, which is now inside metering tube 15g, is carried by the eluate to separation column 17, therein to undergo the stated separation of the ion species contained therein. The effluent from column 17 is led into internal chamber 18b of suppressor 18 and caused to effect cation exchange with the removing solution inside the external chamber 18c through the medium of tube 18a.

As a result, the background of the electric conductivity is degraded. The effluent is then led to detector 19, which detects the electric conductivity thereof and consequently enables a recording meter, not shown, to describe a corresponding chromatogram. The human operator, consulting this chromatogram, turns ON switch valve 21 at the time that the curve of the above $NO_2^-$ ion verges on reaching its peak, so that the internal flow path thereof is shifted from the connected state indicated by the solid line to the connected state indicated by the dotted line in FIG. 2.

As the peak is about to terminate, switch valve 21 is turned OFF by the operator, so that the internal flow path shifts from the connected state indicated by the dotted line to the connected state indicated by the solid line in FIG. 2.

As a result, of the effluent emanating from the detector 21 only the portion that corresponds to the neighborhood of the afore-mentioned $NO_2^-$ ion is introduced via fourth connection port 16d of second switch valve 16, into metering tube 16g.

In this state, when second sample valve 16 is operated so as to shift the connected state indicated by the solid line to the connected state indicated by the dotted line in FIG. 2, the solution inside metering tube 16g is carried by the eluate to separation column 17. In separation column 17, the $NO_2^-$ ion in the solution is separated from the other ion species. Then, the solution is led via internal chamber 18b of suppressor 18, to detector 19, which detects the electric conductivity.

Figure 3:
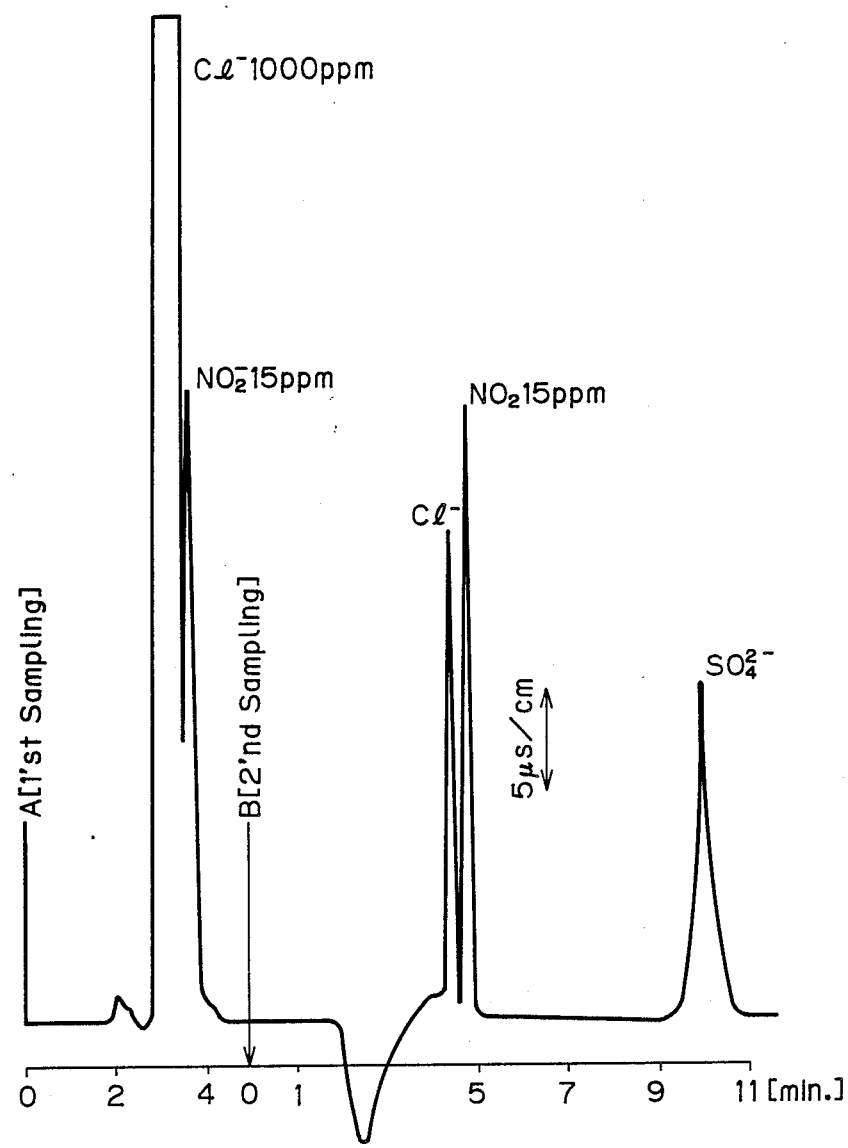
FIGS. 3, 4, 5 are chromatograms obtained by the use of the illustrative embodiment.

FIG. 3 represents a chromatography described in the afore-mentioned recording meter in accordance with the signal consequently fed out by detector 19. In the graph, the horizontal axis represents the scale of elution time of ion (in minutes) and the vertical axis represents the scale of electrical conductivity (in $\mu s/cm$) corresponding to the ion concentration. A represents the duration of the so-called first sampling which is effected when first sample valve 15 is in its switched state. B represents the duration of the so-called second sampling which is effected when a second sample valve 16 is in its switched state.

It is noted from the chromatogram of FIG. 3 that in the first sampling A which corresponds to the general operation of ion chromatography, the separation of $Cl^-$ ion and $NO_2^-$ ion is so poor as to render accurate determination of the $NO_2^-$ ion difficult.

In contrast, in the second sampling B, which is performed in accordance with the invention, the separation of $Cl^-$ ion and $NO_2^-$ ion is effected so efficiently as to enable the determination of $NO_2^-$ ion to be accurately carried out.

Figure 4:
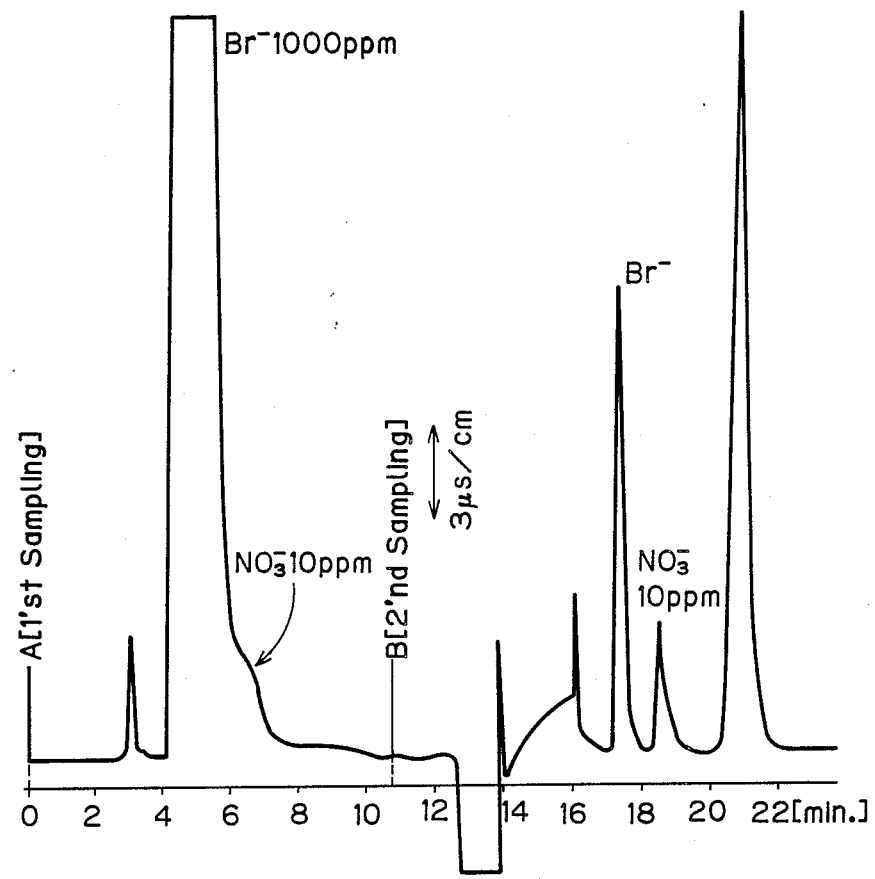
Figure 5:
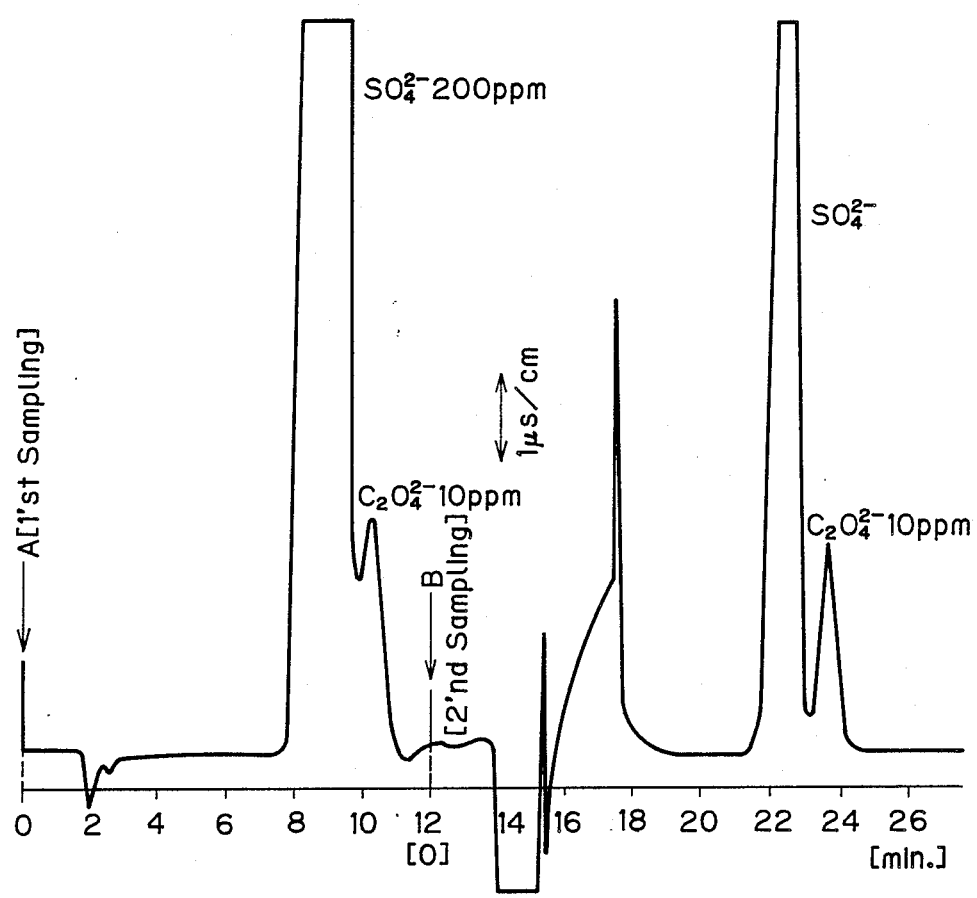

FIGS. 4 and 5 represent chromatograms produced by the use of the illustrative embodiment. The embodiment has separation column 17 suitably charged and filled with appropriate ion exchange resin. These chromatograms are similar to those in FIGS. 3.

FIG. 4 shows data obtained from a solution containing 1000 ppm of $Br^-$ ion and 10 ppm of $NO_3^-$, respectively, as the major constituent and the microconstituent. This graph indicates efficient separation of $NO_3^-$ ion from $Br^-$ ion.

FIG. 5 shows data obtained from a solution containing 2000 ppm of $SO_4^{2-}$ ion and 10 ppm of $C_2O^{4-}$ ion (oxalate ion), respectively, as the maJor constituent and the microconstituent. This graph indicates efficient separation of $C_2O_4^{2-}$ ion from $SO_4^{2-}$ ion.

Figure 6:
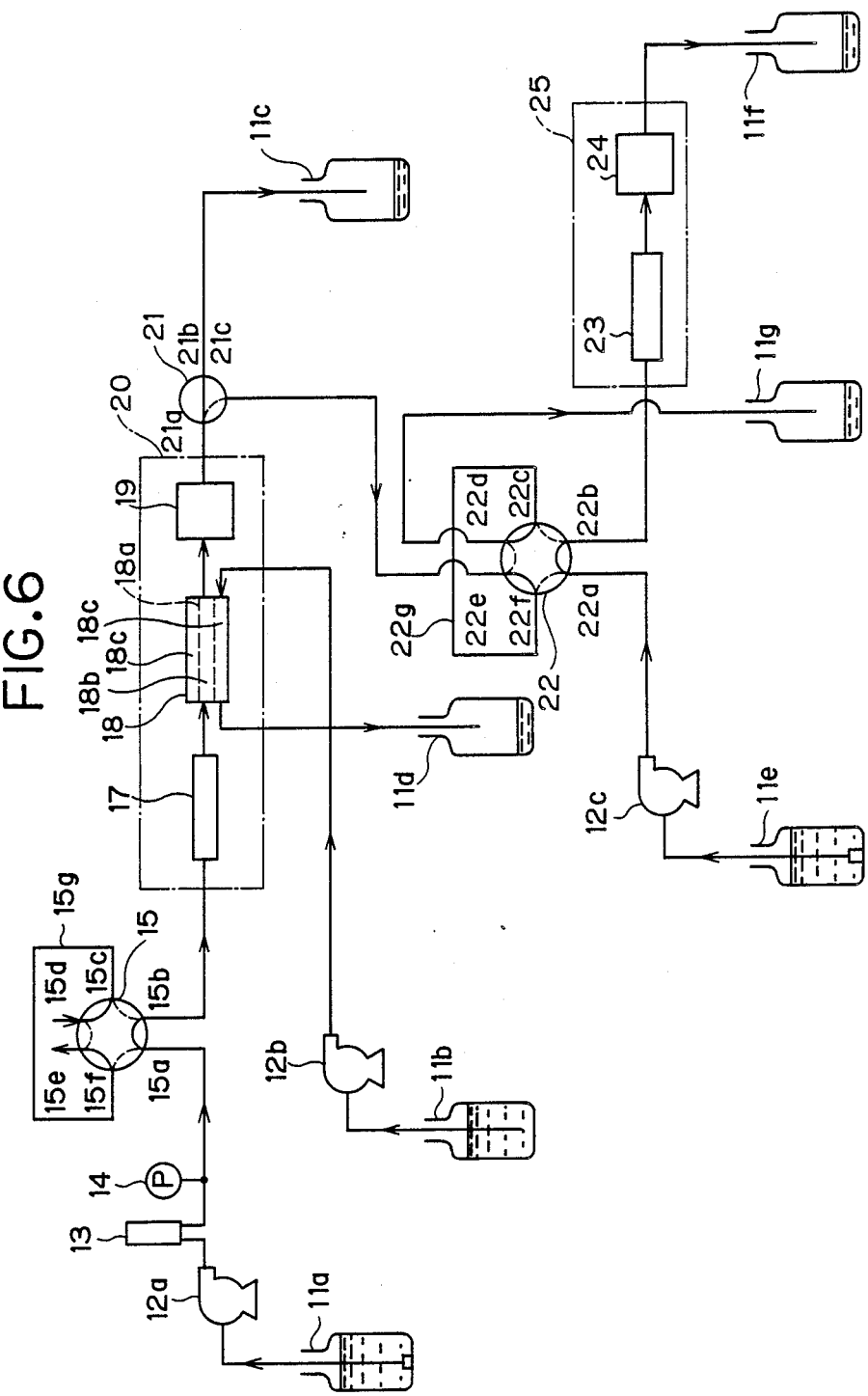
FIG. 6 is an explanatory diagram depicting another illustrative embodiment of the invention.

FIG. 6 depicts another illustrative embodiment of the invention. The same symbols shown in FIG. 2 are used for the same parts and are omitted below from the description for sake of clarity and unnecessary repetition. In this embodiment, a third sample valve 22 is provided comprising first through sixth connection ports 22a–22f and a metering tube 22g and is provided with an internal flow path adapted to be alternately shifted from the connected state indicated by the solid line to the connected state indicated by the dotted line. A separation column 23 is further provided packed with a filler different from the filler of column 17 and adapted to effect separation in a mode different from column 17. Another detector 24 is provided for detecting electric conductivity, for example.

Detector 24 and column 23 are disposed in a constant temperature bath 25 to maintain these components at a prescribed temperature. A further tank 11e is provided for storing an eluate which is pumped by liquid feed pump 12c. Waste liquid tanks 11f and 11g are further provided. Optionally, a suppressor, similar to the suppressor 18 may be interposed between separation column 23 and detector 24. By the use of the second illustrative embodiment of FIG. 6, the solution secured in the second sampling of the embodiment of FIG. 2 can be subjected to separation in separation column 23 which differs in mode of separation from first separation column 17. Thus, a plurality of constituents which are not easily separated by passing the solution twice through first separation column 17 can be advantageously separated.

Switch valve 21, shown in FIGS. 2 and 6, has been described as being switched by the operator while observing the chromatograph produced in the recording meter. The switching operation of switch valve 21 is not limited to the manner described. For example, this operation may be automated by having proper switching intervals set in advance in a sequencer. Further, in the graphs of FIGS. 3 and 4, the peaks of the curves representing microconstituents have been described as riding on the peaks of major constituents. The invention is not limited to this mode of peak discrimination. For example, in a chromatograph of the type having a peak of major constituents riding on the tail of a peak of microconstituents, the so-called front end cut may be effected.

As described in detail above, either of the embodiments of the invention is so constructed as to cause only the portion of the effluent from the detector that corresponds to the neighborhood of the microconstituent to be separated by switch valve 21 and subjected to analysis again. Thus, this invention enjoys the advantage that the microconstituent contained in the major constituent can be easily and quickly determined. It further enJoys the advantage that it possesses universal adaptability of determination and avoids discriminating the microconstituent for determination by its kind because it obviates the necessity of using a selective detector which is indispensible to the above discussed first conventional method, and does not require the solution under testing to be pretreated as contemplated by the above discussed second conventional method.

Moreover, the invention enjoys the advantage that it permits easy automation of the determination process because it is so constructed as to obviate the necessity of using a concentration column as involved in the above discussed third conventional method. Thus, the invention does not require variations in resistance of the solution in the eluate flow path due to use of a concentration column. This particular fact makes the effect of this invention stand out in the light of the fact that any attempt at automating the re-introduction of the fractionated solution in the third conventional method has been generally found to be infeasible. That is, in the third conventional method, the automation of the re-introduction of the fractionated solution inevitably requires incorporation of a special device requiring a pumping function. This special device is susceptible of contamination of the solution being tested. Priorly, solutions to this contamination problem have proven extremely difficult. Thus, the automation of the re-introduction cf the fractionated solution has been generally held to be impracticable. The invention, on the other hand, provides a perfect solution to this problem and enables determination to be easily automated.

The foregoing description is illustrative of the principles of the invention. Numerous modifications and extensions of the invention would be apparent to the worker skilled in the art. All such modifications and extensions are to be considered to be within the spirit and scope of the invention.

What is claimed is:

1. A method for determining a microconstituent in a solution containing such a microconstituent in combination with a major constituent comprising:
   (a) in a first sample valve, collecting a prescribed amount of the solution as a sample and inserting the sample into an eluate carrier using said first sample valve;
   (b) separating the microconstituent and the major constituent from each other by passing the eluate carrier and the sample from the first sample valve through a first separation column comprising a first filler and having a first separation mode for separating the microconstituent from the major constituent to form an effluent containing separated microconstituent and major constituent;

(c) passing the effluent from the first separation column through a suppressor to remove background eluate constituents from the effluent;

(d) detecting the presence of the microconstituent in the effluent from the suppressor with a first detector;

(e) concurrently with detecting the presence of the microconstituent in the effluent from the suppressor, using a switch valve to obtain only a portion of the effluent from the suppressor that approximately corresponds with a detected peak in the presence of the microconstituent;

(f) in a second sample valve, collecting the portion of the effluent obtained in step (e) as a fractionated sample;

(g) separating the microconstituent from the fractionated sample by passing the fractionated sample from the second sample valve through a second separation column without further concentration of the microconstituent, wherein the second separation column comprises a second filler and having a second separation mode for separating the microconstituent, said second separation mode being different from said first separation mode and said second sample valve being interconnected directly and solely between said switch valve and the second separation column; and (h) detecting the presence of the microconstituent in effluent from the second separation column with a second detector.

2. The method of claim 1, wherein the first detector is an electrical conductivity detector.

3. A method for determining a microconstituent in a solution containing such a microconstituent in combination with a major constituent comprising:

(a) in a first sample valve, collecting a prescribed amount of the solution as a sample and inserting the sample into an eluate carrier using said first sample valve;

(b) separating the microconstituent and the major constituent from each other by passing the eluate carrier and the sample from the first sample valve through a separation column to form an effluent containing separated microconstituent and major constituent;

(c) passing the effluent from the separation column through a suppressor to remove background eluate constituents from the effluent;

(d) detecting the presence of the microconstituent in the effluent from the suppressor with a detector;

(e) concurrently with detecting the presence of the microconstituent in the effluent from the suppressor, using a switch valve to obtain only a portion of the effluent from the suppressor that approximately corresponds with a detected peak in the presence of the microconstituent;

(f) in a second sample valve, collecting the portion of the effluent obtained in step (e) as a fractionated sample;

(g) separating the microconstituent from the fractionated sample by passing the fractionated sample from the second sample valve through the separation column without further concentration of the microconstituent; and (h) detecting the presence of the microconstituent in effluent from the separation column obtained in step (g) with the detector.

4. The method of claim 3, wherein the detector is an electrical conductivity detector.